(12) United States Patent
Nishimura et al.

(10) Patent No.: US 12,167,914 B2
(45) Date of Patent: Dec. 17, 2024

(54) SENSOR SHEET

(71) Applicant: Fukuda Denshi Co., Ltd., Tokyo (JP)

(72) Inventors: Naoki Nishimura, Saitama (JP); Yuki Miyauchi, Kochi (JP)

(73) Assignee: Fukuda Denshi Co., Ltd., Tokyo (JP)

( * ) Notice: Subject to any disclaimer, the term of this patent is extended or adjusted under 35 U.S.C. 154(b) by 860 days.

(21) Appl. No.: 15/759,234

(22) PCT Filed: Sep. 8, 2016

(86) PCT No.: PCT/JP2016/076503
§ 371 (c)(1),
(2) Date: Mar. 12, 2018

(87) PCT Pub. No.: WO2017/043595
PCT Pub. Date: Mar. 16, 2017

(65) Prior Publication Data
US 2018/0235502 A1    Aug. 23, 2018

(30) Foreign Application Priority Data

Sep. 11, 2015  (JP) .................................. 2015-179591
Jan. 29, 2016  (JP) .................................. 2016-015909

(51) Int. Cl.
*A61B 5/28*    (2021.01)
*A61B 5/282*   (2021.01)

(52) U.S. Cl.
CPC .............. *A61B 5/28* (2021.01); *A61B 5/282* (2021.01); *A61B 2560/0412* (2013.01);
(Continued)

(58) Field of Classification Search
CPC ............ A61B 5/04087; A61B 5/04085; A61B 5/0422; A61B 2560/0412;
(Continued)

(56) References Cited

U.S. PATENT DOCUMENTS 5,438,984 A * 8/1995 Schoendorfer ...... A61B 5/4845
600/584
5,483,967 A   1/1996 Ohtake
(Continued)

FOREIGN PATENT DOCUMENTS

CN    203169425 U   9/2013
JP    59-116007 U   8/1984
(Continued)

OTHER PUBLICATIONS

Extended European Search Report dated Feb. 19, 2019 for European Patent Application No. 16844456.0.
(Continued)

*Primary Examiner* — Eun Hwa Kim
*Assistant Examiner* — Catherine Premraj
(74) *Attorney, Agent, or Firm* — Shih IP Law Group, PLLC (57) ABSTRACT

Provided is a sensor sheet 100 comprising: a lower sheet 110 that is affixed to the skin of a subject; an upper sheet 120 that is affixed to the surface side of the lower sheet 110; and an electric circuit section 130 provided to an area corresponding to the upper sheet 120. A peripheral edge section 110*a* has a single-layer structure comprising only the lower sheet 110. A central area has a multilayer structure comprising the lower sheet 110 and the upper sheet 120. In this way, the ability to conform to the skin is enhanced in the peripheral edge section 110*a* of the sheet where itching is likely to occur, the electric circuit section 130 can be held firmly in the central area.

8 Claims, 7 Drawing Sheets

(52) U.S. Cl.
CPC . *A61B 2562/0209* (2013.01); *A61B 2562/164* (2013.01); *A61B 2562/222* (2013.01)

(58) Field of Classification Search
CPC ...... A61B 2562/0209; A61B 2562/164; A61B 2562/222; A61B 5/259; A61B 5/282
See application file for complete search history.

(56) References Cited

U.S. PATENT DOCUMENTS

| | | | |
|---|---|---|---|
| 2010/0056881 A1* | 3/2010 | Libbus | A61B 5/085 600/301 |
| 2010/0228113 A1* | 9/2010 | Solosko | A61N 1/0496 600/382 |
| 2011/0077497 A1 | 3/2011 | Oster et al. | |
| 2012/0253162 A1* | 10/2012 | Jones | A61N 1/0472 600/382 |
| 2013/0141093 A1* | 6/2013 | Lang | A61B 5/04087 324/309 |
| 2013/0325096 A1* | 12/2013 | Dupelle | A61N 1/0496 607/142 |

FOREIGN PATENT DOCUMENTS

| | | |
|---|---|---|
| JP | 06-245915 A | 9/1994 |
| JP | 2001-269322 A | 10/2001 |
| JP | 2004-033468 A | 2/2004 |
| JP | 2007-125104 A | 5/2007 |
| WO | 2007/083275 A1 | 7/2007 |

OTHER PUBLICATIONS

International Search Report from International Application No. PCT/JP2016/076503 mailed Dec. 6, 2016.
Office Action mailed Jun. 21, 2023 from EP Application No. 16844456.0, 12 pages.

* cited by examiner

SENSOR SHEET

TECHNICAL FIELD

The present invention relates to a sensor sheet for biological information measurement.

BACKGROUND ART

Conventionally, there are apparatuses that measures biological information of a subject by a sensor sheet with a sensor incorporated therein applied to the body surface of the subject. For example, in the case of electrocardiographic measurement apparatuses, an electrocardiogram of a subject is obtained via electrodes incorporated in a sensor sheet (see Patent Literatures 1 and 2).

In the sensor sheet (biological electric signal recording device) disclosed in Patent Literature 1, electrodes are provided in a sheet-like base material that is flexible enough to follow movements of a living body, and the electrodes are surrounded in a watertight manner by the sheet-like base material, such that measurement of electrocardiograms can be made even during bathing in addition to walking, eating and sleeping.

CITATION LIST

Patent Literature

PTL 1
Japanese Patent Application Laid-Open No. HEI 6-245915
PTL 2
Japanese Patent Application Laid-Open No. 2001-269322

SUMMARY OF INVENTION

Technical Problem

Biological information measurement apparatuses, such as represented by Holter monitors, need a sensor sheet to be continuously applied to a body surface over a long period of time in order to continuously obtain biological information over a long period of time via sensors such as electrodes. For example, in a follow-up after an ablation treatment, continuous data of no less than two weeks is supposed to be obtained, and in this case, it is necessary to continuously apply a sensor sheet to the body surface of a subject over no less than two weeks.

However, when a sensor sheet is continuously applied for many days, the sheet comes off or wrinkles or the surface of the body itches, and thus sensor sheets are generally changed every day or every few days. Therefore, as a result of the sensor sheet changes, the data is temporarily discontinued. Also, there are problems such as inconvenience of changing sensor sheets and wasteful disposal of a sheet equipped with electrodes every time sheets are changed. In addition, the position at which the sensor sheet is applied shifts between before and after a sheet sensor change, and thus the obtained data may be affected by the sheet change and may, for example, fluctuate. Therefore, fewest possible sheet changes are desirable.

Conventionally, sheets that are resistant to coming off for many days have already been provided by giving increased adhesive force of sheets. However, in the conventional sensor sheets, no sufficient consideration has not been given to itching experienced by a subject as a result of such sheets being continuously applied for many days. Here, a main purpose of a sensor sheet is to obtain highly-accurate data, and for that purpose, a sensor sheet needs to be brought into firm and close contact with the body surface, resulting in a dilemma that itching is developed by the firm and close contact.

The present invention has been made in consideration the above points and provides a sensor sheet that can reduce itching experienced by a subject when the sensor sheet is applied to the subject over a long period of time, without decreasing a measurement accuracy.

Solution to Problem

An aspect of the present invention provides a sensor sheet for biological information measurement, the sensor sheet including: a first sheet to be applied to a skin of a subject; a second sheet to be stuck to a front surface side of the first sheet; and a measuring element provided in an area in the second sheet, in which the second sheet is thicker than the first sheet.

Advantageous Effects of Invention

The present invention enables provision of a sensor sheet that can reduce itching experienced by a subject when the sensor sheet is continuously applied to the subject over a long period of time, without decreasing a measurement accuracy.

BRIEF DESCRIPTION OF DRAWINGS

FIGS. 3A, 3B and 3C are diagrams illustrating a configuration of the terminal.

FIGS. 4A and 4B are cross-sectional views for description of a structure of attachment of the terminal to the sensor sheet.

FIGS. 5A and 5B are perspective views for description of an attachment structure in the terminal for attaching the terminal to the sensor sheet.

DESCRIPTION OF EMBODIMENTS

Prior to description of embodiments of the present invention, the manner how the inventors arrived at the present invention will be described. The inventors of the present invention conducted a detailed study on causes of itching when a sensor sheet is applied to the skin. In addition, the inventors conducted a diligent and comprehensive study on a material, a thickness and a placement of a sensor sheet that enable suppressing itching while suppressing a decrease in measurement accuracy.

The study revealed that causes of itching lie largely in the thickness and the moisture vapor permeability in the peripheral edge portion of a sensor sheet.

A reason that intense itching is developed at the edge portion of a sensor sheet when the sheet is applied to the skin can be thought as follows: while the skin can freely expand and contract in a region to which the sheet is not applied, expansion and contraction of the skin are restricted by the sheet in the region to which the sheet is applied, and accordingly, a large difference occurs in expansion and contraction of the skin around the edge portion of the sheet, causing, e.g., a feeling of discomfort and leading to itching. In consideration of this point, in the present invention, in particular, the thickness of the edge portion of a sheet is reduced. As a result of the thickness of the edge portion of a sheet being reduced in this manner, it is possible that itching is less likely to occur even if the sheet is applied for a long time. Also, as a result of the thickness of the edge portion of a sheet being reduced, even if the sheet is tensioned by a movement of the body, the edge portion of the sheet can flexibly follow the movement, the edge portion of the sheet is less likely to wrinkle, and thus the edge portion of the sheet is prevented from coming off. As a result, the prevention of the edge portion of the sheet from coming off leads to suppression of the entire sheet coming off. In other words, the sheet generally starts coming off at the edge portion, but employment of the configuration provided by the present invention enables effectively prevents the edge portion of the sheet from coming off.

Also, for a material of the sheet, polyurethane, which has an excellent moisture vapor permeability, is used. Consequently, a rash caused by sweating is suppressed, enabling further suppression of itching.

Furthermore, in a part other than the edge portion of the sheet, the thickness in the part to which electrodes, wires, gels and a terminal are attached of the sheet is made to be thicker than that of the edge portion. Consequently, the sheet can be prevented from being torn and such components can stably be held.

A sensor sheet according to the present invention is a sensor sheet ensuring all of itching prevention, prevention of the sheet coming off and stable holding of mounted components.

Embodiments of the present invention will be described in detail below with reference to the accompanying drawings.

<1> Embodiment 1

<1-1> Overall Configuration

Figure 1:
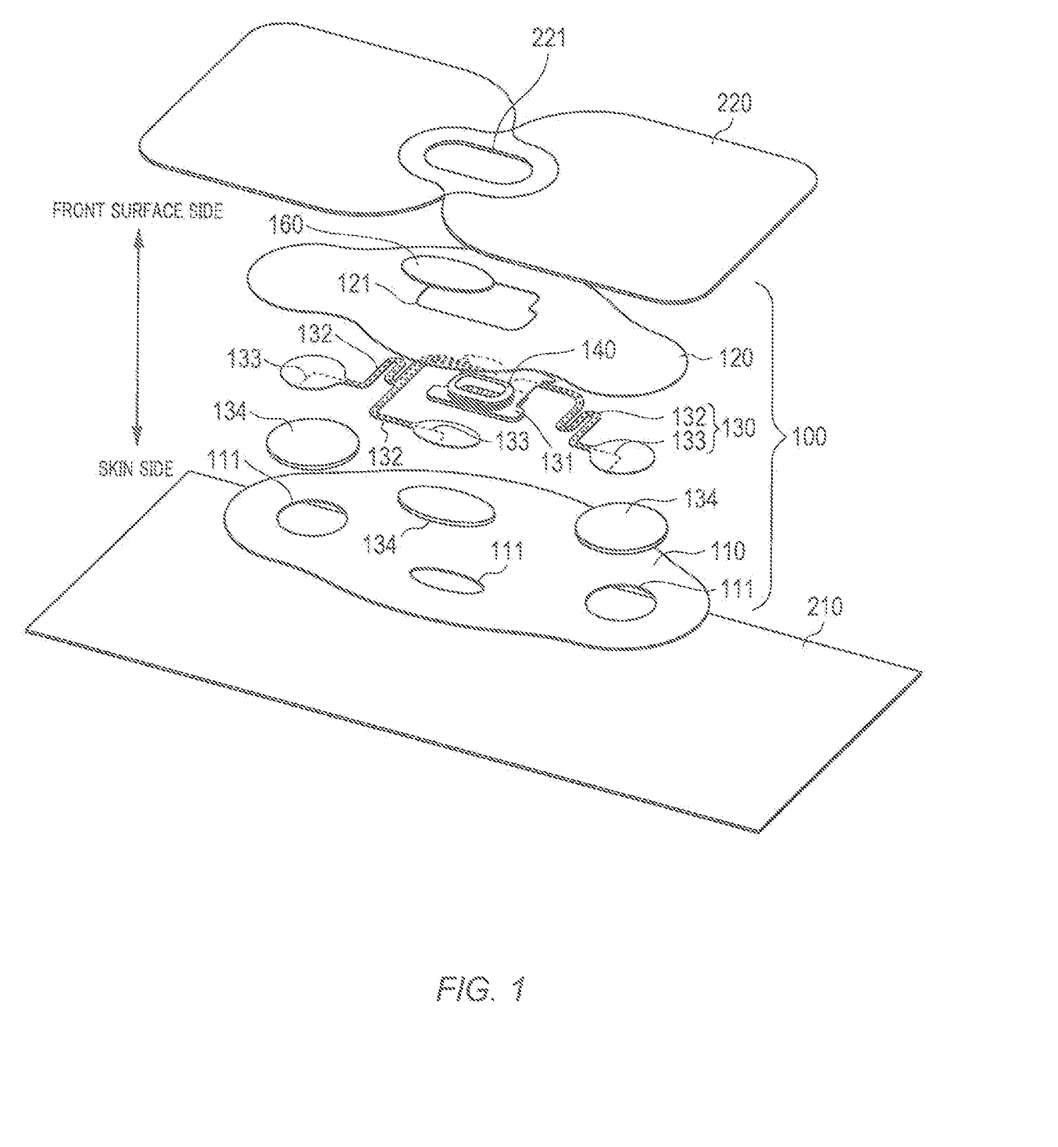
FIG. 1 is an exploded perspective view illustrating an overall configuration of a sensor sheet according to Embodiment 1.
Figure 2:
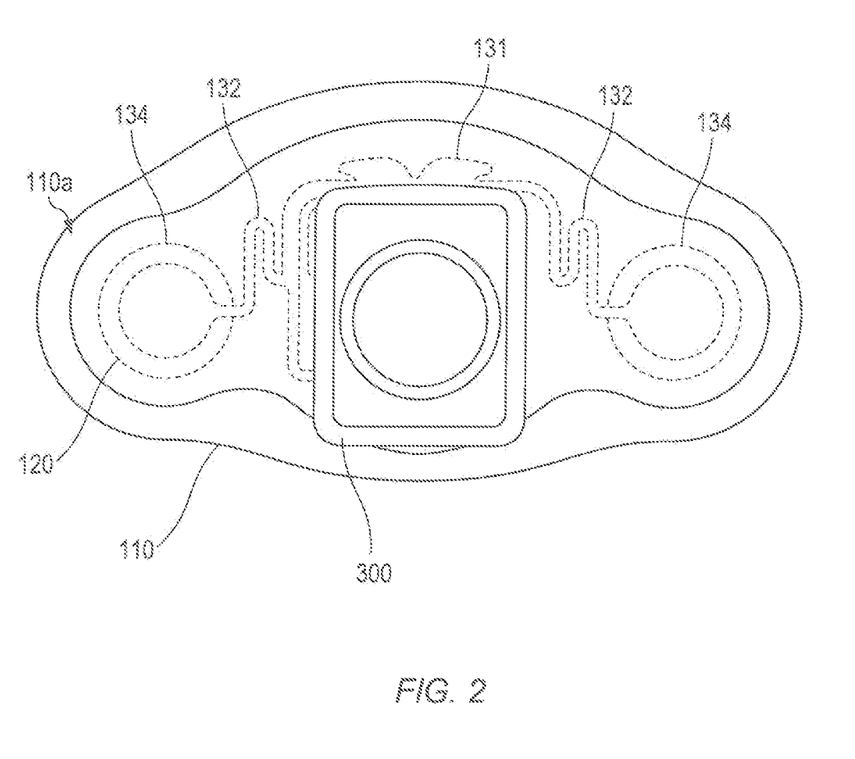
FIG. 2 is a top view of the sensor sheet according to Embodiment 1 with a terminal is attached thereto.

FIG. 1 is an exploded perspective view illustrating an overall configuration of a sensor sheet according to Embodiment 1 of the present invention. FIG. 2 is a top view of the sensor sheet with a terminal attached thereto. The sensor sheet is attached to the chest region of a subject and used to obtain an electrocardiogram.

The present embodiment will be described in terms of a case where a terminal to be attached to a sensor sheet is a recording terminal including a memory and a coin cell housed inside a case thereof; however, the terminal to be attached to the sensor sheet is not limited to this type of terminal. For example, the terminal may be a terminal that includes a wireless transmission section inside a case and wirelessly transmits biological information measured by the sensor sheet. Also, the terminal may be, for example, a telemeter.

As illustrated in FIG. 1, before use, sensor sheet 100 is held between liner 210 and top separator 220. Then, in use, liner 210 and top separator 220 are removed and sensor sheet 100 is applied to the chest region, and as illustrated in FIG. 2, terminal 300 is attached to the front surface side.

Sensor sheet 100 includes lower sheet (first sheet) 110 and upper sheet (second sheet) 120. Electric circuit section 130, which serves as a measuring element, is disposed between lower sheet 110 and upper sheet 120. An adhesion layer is provided on a surface on the skin side of each of lower sheet 110 and upper sheet 120, and consequently, lower sheet 110 is to be applied to the skin of a subject and upper sheet 120 is stuck to the front surface side of lower sheet 110. Electric circuit section 130 is held between lower sheet 110 and upper sheet 120 as a result of upper sheet 120 being stuck to the front surface side of lower sheet 110.

Upper sheet 120 is smaller in area than lower sheet 110. The area of upper sheet 120 is large enough to cover electric circuit section 130. More specifically, as can be seen from FIG. 2, which illustrates upper sheet 120 stuck to lower sheet 110, peripheral edge portion 110a, which is formed of lower sheet 110 alone, is formed over an entire circumference of sensor sheet 100 while electric circuit section 130 is fully covered by upper sheet 120.

Electric circuit section 130 includes tongue piece 131, a plurality of wires 132 extending from tongue piece 131, and a plurality of electrodes 133 formed at terminal ends of respective wires 132.

Holes 111 are formed at positions in lower sheet 110 that correspond to respective electrodes 133, and gels 134 are disposed at positions corresponding to respective holes 111. Consequently, electrodes 133 are electrically connected to the skin via gels 134, and electric conductivity between the skin and electrodes 133 is enhanced by gels 134.

Connector 140 to be connected to terminal 300 is provided on the front surface side of tongue piece 131. Hole 121 is formed at a position in upper sheet 120, the position corresponding to tongue piece 131. Consequently, in a state in which upper sheet 120 is stuck to lower sheet 110, tongue piece 131 is exposed on the front surface side of upper sheet 120 via hole 121.

Furthermore, hole 221 is formed at a position in top separator 220, the position corresponding to connector 140. Consequently, connector 140 is exposed on the front surface side of top separator 220 via hole 221.

Here, lower sheet 110 includes a base material formed of polyurethane and the adhesion layer formed on the surface on the skin side of the base material. Likewise, upper sheet 120 includes a base material formed of polyurethane and the adhesion layer formed on the surface on the skin side of the base material. As described above, sheets 110, 120 are each formed of polyurethane having a high moisture vapor permeability, enabling suppression of a skin rash caused by sweating and thus enabling suppression of itching caused by a rash.

For further information, polyurethane has the characteristic of transmitting water vapor and not transmitting collected water (that is, transmitting small particles such as water vapor, but not transmitting a large mass of water such as collected water or a water droplet), and thus, when the subject takes a bath, there is almost no permeation of water from the front surface side to the skin side of upper sheet 120. Therefore, entry of water from the front surface side of upper sheet 120 to wires 132 and electrodes 133 can be suppressed, enabling prevention of a short in the electric circuit even when the subject takes a bath with sensor sheet 100 applied.

Although in the present embodiment, lower sheet 110 and upper sheet 120 are both formed of polyurethane, itching is likely to occur particularly at a peripheral edge portion of a sheet, and thus, it is possible that: only lower sheet 110 including peripheral edge portion 110a is formed of polyurethane; and upper sheet 120 is formed of a material other than polyurethane. Furthermore, for materials of lower sheet 110 and upper sheet 120, any of various materials other than polyurethane can be used as long as such materials are ones that can prevent entry of water that causes a short in wires 132 and electrodes 133 while transmitting moisture resulting from sweating. For example, foamed polyethylene or a non-woven material may be used. Also, lower sheet 110 and upper sheet 120 are not necessarily formed of polyurethane alone, and may be formed of a material containing polyurethane as a main component.

However, the inventors found out that polyurethane is most excellent for materials of lower sheet 110 and upper sheet 120. Here, for lower sheet 110 and upper sheet 120, for example, almost no permeation of water from the front surface side to the skin side of upper sheet 120 when the subject takes a bath (that is, waterproof property), the capability of being used for a long period of time without being torn (that is, durability), a flexibly enabling following movements of the skin (that is, stretchability), and the capability of being thinned are required. Polyurethane is desirable in all of waterproof property, durability, stretchability and the capable of being thinned On the other hand, foamed polyethylene is poor in durability and the capability of being thinned. Non-woven fabric is poor in waterproof property.

Lower sheet 110 in the present embodiment has a thickness of 15 [μm]. This thickness is much smaller than a thickness of around 50 [μm], which is a thickness of a conventional sheet of this type. On the other hand, upper sheet 120 has a thickness that is larger than that of lower sheet 110. In the case of the present embodiment, upper sheet 120 has a thickness of 50 [μm]. In other words, in the case of the present embodiment, while peripheral edge portion 110a formed of lower sheet 110 alone has a thickness of 15 [μm] and thus, is very thin, a center area in which electric circuit section 130 is held has a thickness of 65 [μm] including the thicknesses of lower sheet 110 and upper sheet 120. Consequently, even if peripheral edge portion 110a is very thin, the center area in which electric circuit section 130 is held is thick, enabling a measurement accuracy decrease to be prevented without a decrease in reliability of electric circuit section 130.

In particular, it is desirable that upper sheet 120 be made to be thicker than lower sheet 110. In other words, it is only necessary to form upper sheet 120 so as to be higher in strength than lower sheet 110. For example, upper sheet 120 may be formed of a material having a strength that is higher than that of lower sheet 110.

The reason why a conventional sheet has a large thickness including a peripheral edge portion thereof is that a priority is placed on suppression of damage of the sheet and highly reliable holding of electric circuit section 130, which serves as a measuring element, and no sufficient consideration is given to itching caused when the sheet is continuously applied for a long period of time.

In the present invention, as described above, paying attention to the point that itching can substantially be reduced if peripheral edge portion 110a follows the skin, lower sheet 110 was studied in terms of material and thickness. As a result, it has been found that if lower sheet 110 is formed of polyurethane in consideration of moisture vapor permeability, itching is less likely to occur even if lower sheet 110 is continuously applied for around two weeks as long as lower sheet 110 has a thickness of no more than 20 [μm]. In other words, in the present embodiment, forming lower sheet 110 from polyurethane and making lower sheet 110 have a thickness of no more than 20 [μm] are proposed.

Also, as described above, lower sheet 110 is made to have a very small thickness of no more than 20 [μm] and is thus superior in following the skin, which provides the advantage of enabling provision of a sheet that is less likely to come off in addition to suppression of itching. In other words, a sheet almost always starts coming off at a peripheral edge portion and thus, can be prevented from coming off by the configuration provided by the present embodiment.

Wires 132 and electrodes 133 are configured by forming a metal layer on a base material formed of, e.g., PET (polyethylene terephthalate) or PEN (polyethylene naphthalate). The base material has a thickness of, for example, around 50 to 100 [μm]. It is also possible that wires 132 and electrodes 133 are formed directly on upper sheet 120 or lower sheet 110; however, in the case of the present embodiment, wires 132 and electrodes 133 are formed on, e.g., the base material formed of, e.g., PET (polyethylene terephthalate) or PEN (polyethylene naphthalate), enabling prevention of occurrence of, e.g., disconnection.

Here, the base material formed of, e.g., PET (polyethylene terephthalate) or PEN (polyethylene naphthalate) is less flexible than polyurethane, which is the material of lower sheet 110 and upper sheet 120. Therefore, in the case of the present embodiment, wires 132 have a pattern including a meandering pattern. Consequently, wires 132 follows movements of the body surface (skin) well. As a result, the capability of following the skin can be enhanced also in the area of electric circuit section 130, as well as peripheral edge portion 110a, enabling further suppression of occurrence of itching. However, wires 132 do not necessarily need to be made to meander, and wires 132 may be formed in a shallow curve or a linear fashion.

Tongue piece 131 is thicker than the base material of wires 132 and electrodes 133. Terminal 300 is detachably attached to connector 140 provided on tongue piece 131. A structure of the attachment of connector 140 to terminal 300 will be described later.

Next, a procedure for applying sensor sheet 100 to the chest region of a subject will be described.

When sensor sheet 100 is applied to a predetermined position in the chest region, first, liner 210 is removed and sensor sheet 100 is pressed against the predetermined position in the chest region together with top separator 220 to apply lower sheet 110 to the predetermined position in the chest region.

Top separator 220 is rubbed from above in this state, whereby lower sheet 110 is firmly applied to the skin of the subject. For further information, an adhesion layer having a small adhesive force enough to hold sensor sheet 100 is formed on a lower surface of top separator 220.

The provision of top separator 220 enables prevention of twisting of peripheral edge portion 110a of very thin lower sheet 110. Hole 221 for avoiding connector 140 is formed at a center of top separator 220. A user holds areas in the periphery of hole 221 between his/her fingers and separate and peel back top separator 220 so as to be separated and removed outward like opening a double door, whereby top separator 220 is removed from sensor sheet 100. As described above, as a result of top separator 220 being removed from sensor sheet 100 from the center to the edge side of sensor sheet 100, rather than from the edge side, lower sheet 110 is strained by top separator 220, enabling reduction in possibility of the edge of lower sheet 110 peeling off and wrinkling.

After sensor sheet 100 is applied to the chest region to the subject in this way, the user attaches terminal 300 to connector 140 of sensor sheet 100.

<1-2> Structure of Attachment of Terminal 300 to Sensor Sheet 100

Figure 3A:
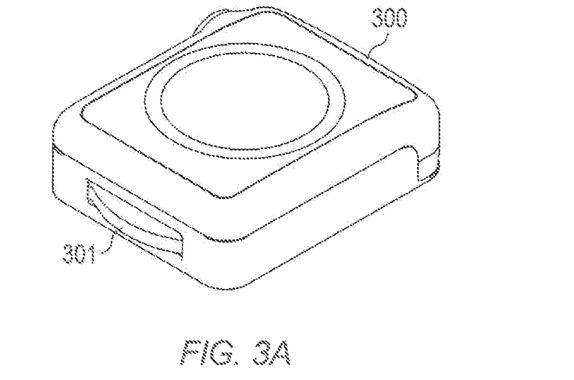
FIG. 3A is a perspective view.
Figure 3B:
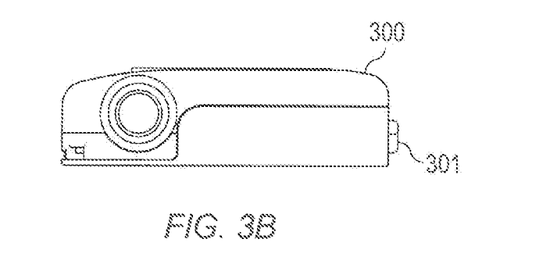
FIG. 3B is a side view.
Figure 3C:
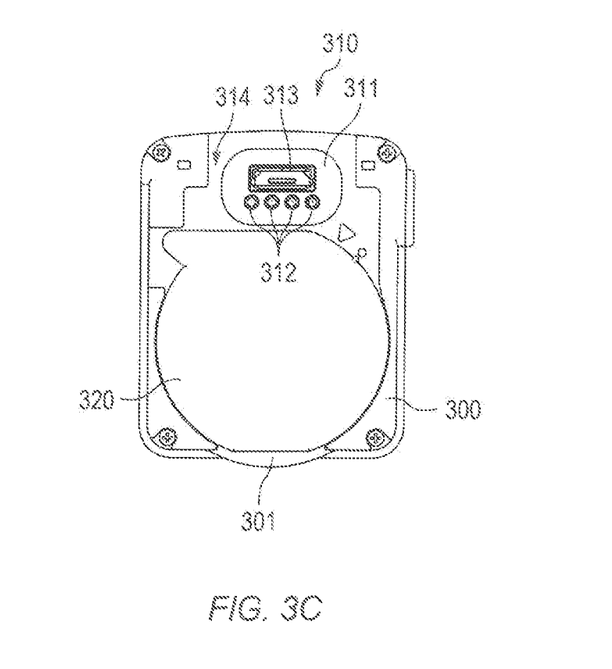
FIG. 3C is a bottom view.

FIGS. 3A, 3B and 3C are diagrams illustrating a configuration of terminal 300; FIG. 3A is a perspective view, FIG. 3B is a side view and FIG. 3C is a bottom view.

Terminal 300 includes, e.g., a coin cell and a memory incorporated therein. Upon power supply button 301 being pressed, terminal 300 starts an electrocardiographic measurement and recording operation, and records an electrocardiogram based on an electrocardiographic signal from the sensor sheet. This measurement and recording operation is a known technique and thus, description thereof will be omitted.

As illustrated in FIG. 3C, attachment section 310 to be detachably attached to connector 140 provided in sensor sheet 100 is provided in a back surface of terminal 300.

Figure 4A:
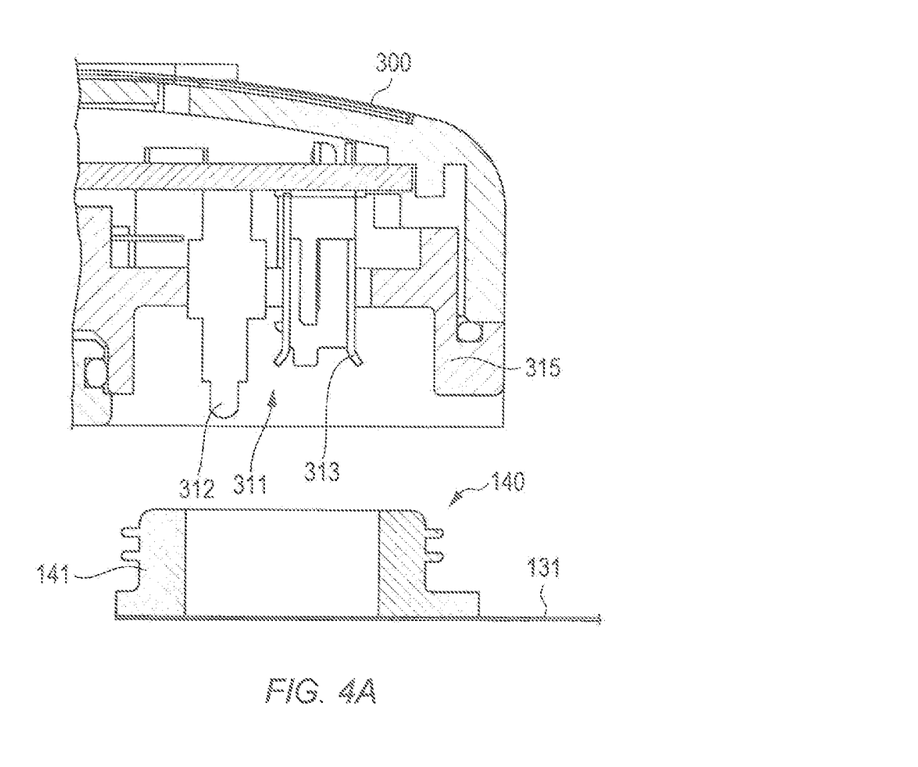
FIG. 4A is a cross-sectional view before attachment.
Figure 4B:
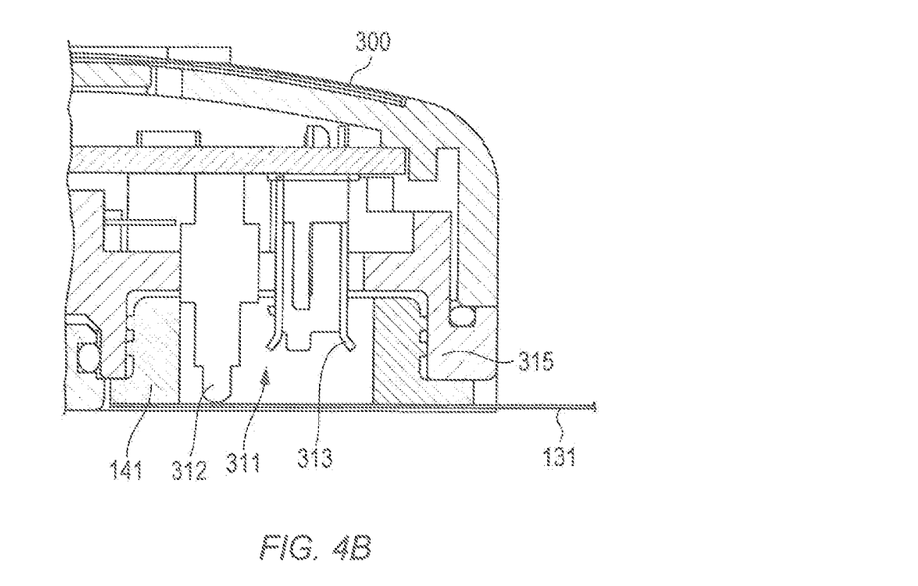
FIG. 4B is a cross-sectional view after attachment.

FIGS. 4A and 4B are cross-sectional views for description of a structure of attachment of terminal 300 to sensor sheet 100. FIG. 4A is a cross-sectional view before attachment, and FIG. 4B is a cross-sectional view after attachment.

Figure 5A:
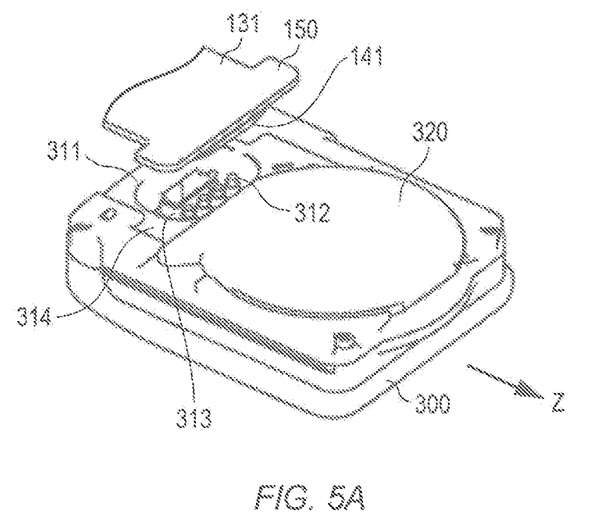
FIG. 5A is a cross-sectional view before attachment.
Figure 5B:
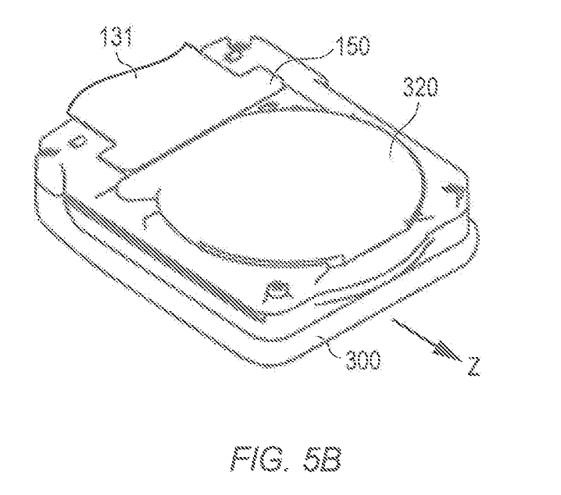
FIG. 5B is a cross-sectional view after attachment.

FIGS. 5A and 5B are perspective views for description of a structure of attachment of terminal 300 to sensor sheet 100; FIG. 5A is a perspective view before attachment, and FIG. 5B is a perspective view after attachment.

Here, connector 140 provided on the sensor sheet 100 side includes packing 141 having an oval shape in plan view. Terminal ends of wires 132, other ends of which are connected to respective electrodes 133, are disposed on an area in tongue piece 131, the area being surrounded by packing 141.

Also, insertion opening 311 having a size that allows packing 141 to be just fitted therein is formed in the back surface of terminal 300. Inside insertion opening 311, spring probes 312 and USB port 313 are disposed.

Consequently, as illustrated in FIG. 4B, upon insertion of packing 141 to insertion opening 311 in the back surface of terminal 300, spring probes 312 are brought into abutment with the terminal ends of wires 132, the terminal ends being exposed on tongue piece 131, at a predetermined pressure, whereby the spring probes 312 and the wires 132 are electrically interconnected, respectively. Also, in this state, the inner side surrounded by packing 141 is prevented from entry of water from the outside. In other words, the plurality of spring probes 312 and the plurality of wires 132 are electrically connected without short-circuiting caused by water.

Furthermore, inside insertion opening 311, USB port 313 is disposed in addition to spring probes 312, and thus, when electrocardiographic measurement is being performed with terminal 300 attached to sensor sheet 100, USB port 313 cannot be used. Consequently, the risk of electrical shock caused by connection of an external electronic device to USB port 313 during electrocardiograph measurement can reliably be eliminated. In other words, in the present embodiment, the contacts for electrocardiographic measurement (spring probes 312) and USB port 313 are prevented from being connected simultaneously to ensure safety. Furthermore, the contacts for electrocardiographic measurement (spring probes 312) and USB port 313 are housed inside packing 141 and are thus waterproofed at the same time. In other words, both waterproofing and safety can be ensured by the simple configuration.

Furthermore, as illustrated in FIGS. 5A and 5B, wide portion 150 is formed at a distal end of tongue piece 131. Also, locking cut 314 is formed in the back surface of terminal 300. Upon insertion of packing 141 of connector 140 to insertion opening 311, wide portion 150 of tongue piece 131 engages with locking cut 314, whereby terminal 300 is locked by tongue piece 131 so as not to move in the arrow Z direction (direction around the ground where terminal 300 is attached).

Furthermore, hook-and-loop fastener 160 is firmly fixed to the front surface side of upper sheet 120. Hook-and-loop fastener 160 can be joined to hook-and-loop fastener 320 provided on the back side of terminal 300.

Consequently, upon insertion of packing 141 to insertion opening 311, terminal 300 is held on sensor sheet 100 by engagement between tongue piece 131 and locking cut 314 and joining between hook-and-loop fasteners 160, 320. Here, hook-and-loop fasteners 160, 320 have only a small holding force in a direction perpendicular to the surface, but have a large force in the surface direction. Therefore, tongue piece 131 and hook-and-loop fasteners 160, 320 reliably prevent terminal 300 from dropping in the surface direction.

Here, terminal 300 engages with tongue piece 131 at an upper portion and thereby hang down with tongue piece 131 as an axis. Upon terminal 300 being lightly pushed to the sensor sheet 100 side (that is, the subject side) in this state, hook-and-loop fasteners 160, 320 are joined to each other and terminal 300 are thereby prevented from wobbling. In fact, terminal 300 is held by tongue piece 131 so as to be at least partly floated from sensor sheet 100.

The subject perceives terminal 300 via the skin at the part of the joining between tongue piece 131 and the packing 141 and the part of the joining between hook-and-loop fasteners 160, 320, and as a result, for example, a feeling of discomfort the subject have due to the presence of terminal 300 can be reduced compared to a case where the entire back surface of terminal 300 is firmly fixed to sensor sheet 100. A further decrease in area of hook-and-loop fasteners 160, 320 enables further reduction of a feeling of discomfort the subject has.

Furthermore, hook-and-loop fastener 160 is disposed at a position corresponding to gel 134. Consequently, the gel serves as a buffer, which makes the subject be less likely to feel the presence of terminal 300.

Instead of hook-and-loop fasteners 160, 320, for example, a snap fastener or magnets may be used. In brief, any various rejoinable joining devices can be used.

<1-3> Advantageous Effects of Embodiment 1

As described above, according to the present embodiment, lower sheet (first sheet) 110 to be applied to the skin of a subject, upper sheet (second sheet) 120 stuck to the front surface side of lower sheet 110, and electric circuit section (measuring element) 130 provided in an area corresponding to upper sheet 120 are provided, peripheral edge portion 110a has a single-layer structure including lower sheet 110 alone, and the center area has a multi-layer structure including lower sheet 110 and upper sheet 120, whereby while the capability of following the skin is enhanced in sheet peripheral edge portion 110a, which is likely to cause itching, electric circuit section (measuring element) 130 can firmly be held in the center area, and thus, sensor sheet 100 that can reduce itching experienced by the subject when sensor sheet 100 is continuously applied to the subject over a long period of time can be provided without decreasing measurement accuracy. In particular, sensor sheet 100 can significantly reduce itching experienced by a subject when sensor sheet 100 is applied to the subject for no less than two weeks, compared to conventional sensor sheets.

Also, as a result of upper sheet (second sheet) 120 being made to be thicker than lower sheet (first sheet) 110, electric circuit section (measuring element) 130 can more firmly be held while the capability of following the skin is further be enhanced in sheet peripheral edge portion 110a.

Also, as a result of lower sheet 110 being formed of a material containing polyurethane as a main component and being made to have a thickness of no more than 20 [μm], itching can further be reduced.

Although Embodiment 1 above has been described in terms of a sensor sheet according to the present invention in which all of electrodes 133 are held inside single sheets 110, 120, the present invention is applicable to a sheet in which in electrodes 133 are disposed on individual sheets and electrodes 133 are interconnected via lead wires to be not applied to a subject. However, in Embodiment 1 above, electrodes 133, wires 132 and tongue piece 131 are integrally formed, and thus, a signal with small noise can be obtained in comparison to a configuration in which electrodes 133, wires 132 and tongue piece 131 are formed separately and interconnected via cables or connection sections.

Also, although Embodiment 1 above has been described in terms of the case where electric circuit section 130 including, e.g., wires 132 and electrodes 133 is mounted in sensor sheet 100, a measuring element mounted in a sensor sheet according to the present invention is not limited to electric circuit section 130. For example, an optical component for measuring $SpO_2$ may be mounted. A sensor sheet according to the present invention may be employed as a sensor sheet for measuring any of various types of biological information if a measuring element mounted in the sensor sheet is selected according to the object to be measured.

Also, although Embodiment 1 above has been described in terms of the case where electric circuit section 130, which serves as a measuring element, is disposed between lower sheet 110 and upper sheet 120, a measuring element may be disposed on upper sheet 120.

Also, although Embodiment 1 above has been described in terms of the case where the center area of sensor sheet 100 has a multi-layer structure including lower sheet 110 and upper sheet 120, the center area may have a single-layer structure including upper sheet 120 alone with no lower sheet 110 provided. Even in such case, upper sheet 120 is made to be higher in strength than lower sheet 110, enabling provision of both a force for holding the measuring element in the center area and the capability of following the skin in peripheral edge portion 110a.

Also, although Embodiment 1 above has been described in terms of the case where tongue piece 131 is formed separately from upper sheet 120, tongue piece 131 may be formed integrally with upper sheet 120. In other words, tongue piece 131 may be provided so as to extend from upper sheet 120.

Furthermore, although Embodiment 1 above has been described in terms of a case where a sensor sheet according to the present invention is applied to the chest region of a subject in use, a sensor sheet according to the present invention may be applied not only to the chest region, but also regions other than the chest region, such as the abdominal region or the back, of a subject in use. In brief, a sensor sheet according to the present invention can arbitrarily be applied to a region suitable for obtainment of biological information.

These points are applicable also to Embodiment 2 described below.

<2> Embodiment 2

<2-1> Overall Configuration

Figure 6:
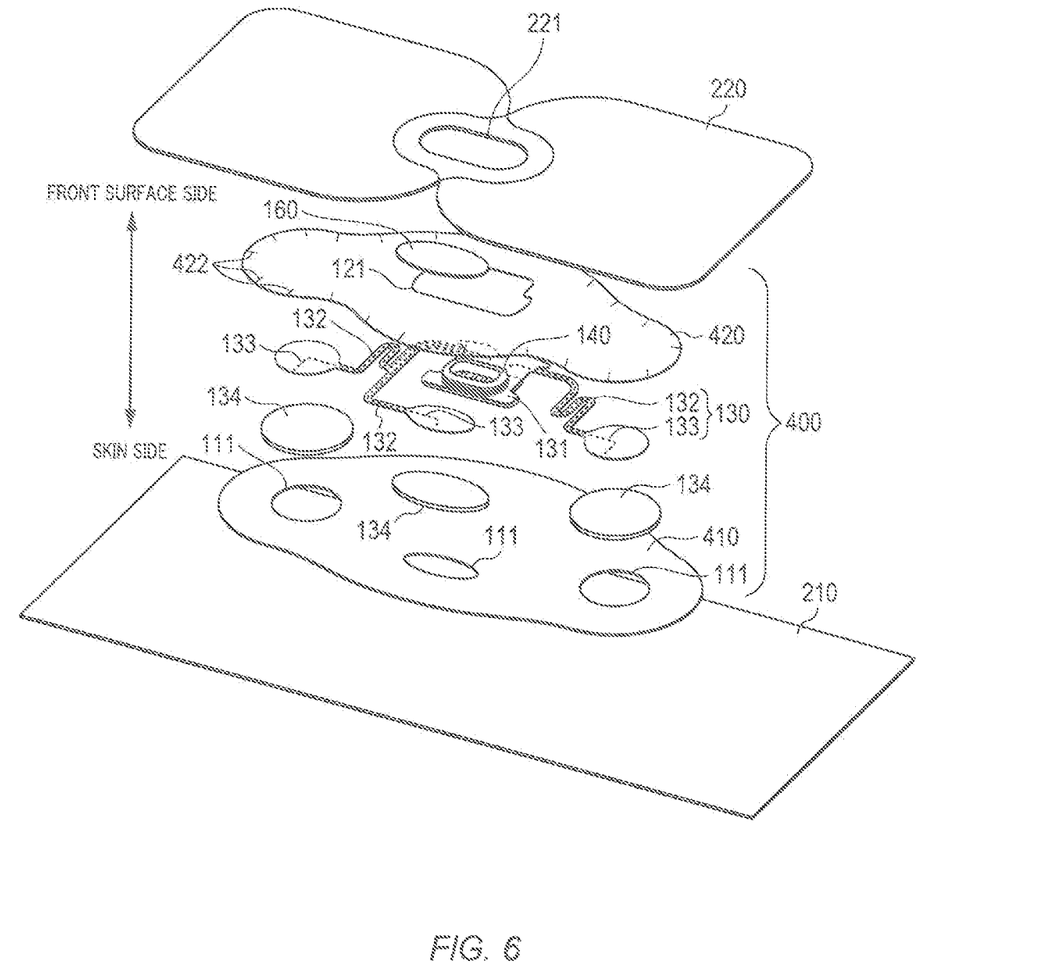
FIG. 6 is an exploded perspective view illustrating an overall configuration of a sensor sheet according to Embodiment 2.
Figure 7:
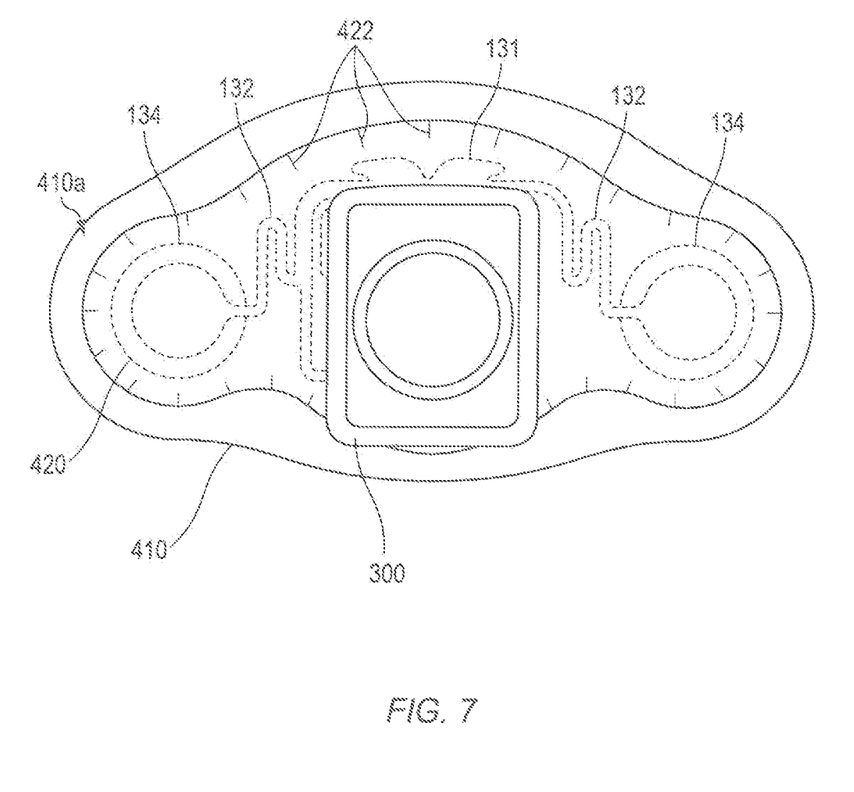
FIG. 7 is a top view of the sensor sheet according to Embodiment 2 with a terminal attached thereto.

FIG. 6, which illustrates parts corresponding to parts in FIG. 1 with reference numerals that are the same as those in FIG. 1 provided thereto, is an exploded perspective view illustrating an overall configuration of a sensor sheet according to Embodiment 2. FIG. 7 is a top view of the sensor sheet according to Embodiment 2 with a terminal attached thereto.

In sensor sheet 400 according to the present embodiment, lower sheet 410 is higher in stretchability than upper sheet 420, and consequently, even if the sheet is tensioned by a movement of the body, peripheral edge portion 410a having a high stretchability flexibly follows the movement, enabling suppression of itching, wrinkling, and coming-off of the sheet at an edge portion thereof.

In addition to such configuration, a plurality of slits 422 are formed in an edge portion of upper sheet 420. Slits 422 are formed over an entire circumference of the edge portion. Slits 422 are formed so as to extend in a direction toward a center of upper sheet 420, which is perpendicular to a direction of a tangent to the edge portion. An interval and a length of slits 422 may arbitrarily be determined according to, e.g., a difference in stretchability between lower sheet 410 and upper sheet 420. For example, it is possible that as the difference in stretchability is larger, slits 422 are longer or the interval of slits 422 is shorter. Also, the length and the interval of slits 422 do not need to be constant over the entire circumference. In the case of the present embodiment, the interval of slits 422 is 5 mm, and the length of slits 422 is 2 mm As described above, as a result of slits 422 being formed in upper sheet 420, upper sheet 420 coming off from lower sheet 410 can be suppressed. In other words, in the present embodiment, the stretchability of lower sheet 410 is made to be higher than that of upper sheet 420, and thus, a difference in stretch occurs between lower sheet 410 and upper sheet 420, and as a result, when sensor sheet 400 is continuously applied to the body surface over a long period of time, upper sheet 420 may come off from lower sheet 410. Such coming-off is highly likely to start at the edge portion of upper sheet 420 at which the stretchability sharply changes. Therefore, in the present embodiment, slits 422 are formed in the edge portion of upper sheet 420 to moderate such sharp stretchability change and thereby suppress upper sheet 420 coming off from lower sheet 410. In the present embodiment, slits 422 make a peripheral edge area of upper sheet 420 be a buffer area having a stretchability that is lower than that of lower sheet 410 and higher than that of a center area of upper sheet 420.

As a result of provision of slits 422, a shear stress caused by the stretchability difference, the shear stress causing two types of sheets to come off from each other, is reduced by slits 422. For further information, the slit parts partially come off, but the degree of the coming-off is such that sensor sheet 400 can sufficiently function as an electrocardiographic electrode. If no slits 422 are provided, the coming-off may become large and develop to the degree that the sensor sheet 400 cannot sufficiently function as an electrocardiographic electrode, for example, lower sheet 410 and upper sheet 420 may be separated from each other.

Although in the present embodiment, slits 422 are formed in the edge portion of upper sheet 420, the present invention is not limited to this case, and in brief, the stretchability of peripheral edge area of upper sheet 420 just needs to be higher than that of the center area of upper sheet 420. Therefore, for example, the peripheral edge area of upper sheet 420 may be formed of a material having a stretchability that is higher than that of the center area of upper sheet 420 or a thickness of the peripheral edge area of upper sheet 420 may be made to be smaller than that of the center area of upper sheet 420.

<2-2> Advantageous Effects of Embodiment 2

As described above, according to the present embodiment, in addition to the configuration of Embodiment 1, in consideration of lower sheet (first sheet) 410 having a high stretchability than that of an area in upper sheet (second sheet) 420, the stretchability of the peripheral edge area of upper sheet (second sheet) 420 is made to be higher than that of the center area of upper sheet (second sheet) 420, enabling suppression of upper sheet (second sheet) 420 coming off from lower sheet (first sheet) 410. As a result, more reliable measurement can be performed.

Sensor sheet 400 according to the present embodiment is a sensor sheet for biological information measurement, the sensor sheet including:

a first sheet to be applied to a skin of a subject; a second sheet stuck to a center area on a front surface side of the first sheet except a peripheral edge area of the first sheet; and a measuring element provided on an area in the second sheet, wherein the first sheet is higher in stretchability than the second sheet, and the stretchability of a peripheral edge area of the second sheet is higher than that of a center area of the second sheet.

In sensor sheet 400 according to the present embodiment, the peripheral edge area of the second sheet is a buffer area having a stretchability that is lower than that of the first sheet and higher than that of the center area of the second sheet.

Sensor sheet 400 according to the present embodiment includes slits formed in the peripheral edge area of the second sheet.

In sensor sheet 400 according to the present embodiment, the peripheral edge area of the second sheet is formed of a material having a stretchability that is higher than that of the center area of the second sheet.

Also, although Embodiments 1 and 2 above have been described in terms of a case where an upper sheet (second sheet) is smaller in area than a lower sheet (first sheet), the present invention is not necessarily limited to this case. For example, where a second sheet is attached to a first sheet in such a manner that the second sheet is folded, the second sheet may be larger in area than the first sheet, and the prevent invention is also effective in such case. In other words, the present invention is widely effective for cases where a second sheet is attached to a center area on the front surface side of a first sheet except a peripheral edge area of the first sheet.

Embodiments 1 and 2 are mere specific examples for carrying out the present invention and the technical scope of the present invention should not be limited by these embodiments. In other words, the present invention can be carried out in various modes without departing from the spirit or the main features of the invention.

The present application claims priority based on Japanese Patent Application No. 2015-179591 filed on Sep. 11, 2015 and Japanese Patent Application No. 2016-015909 filed on Jan. 29, 2016. The entire disclosures in the descriptions and the drawings in these applications are incorporated herein by reference.

INDUSTRIAL APPLICABILITY

The present invention is suitable for, for example, a sensor sheet for measuring biological information that needs to be measured over a long period of time.

REFERENCE SIGNS LIST

100, 400 sensor sheet
110, 410 lower sheet
110a, 410a peripheral edge portion
120, 420 upper sheet
130 electric circuit section
131 tongue piece
132 wire
133 electrode
134 gel
140 connector
141 packing
150 wide portion
160, 320 hook-and-loop fastener
210 liner
220 top separator
300 terminal
310 attachment section
311 insertion opening
312 spring probe
313 USB port
314 locking cut

The invention claimed is:

1. A sensor sheet for biological information measurement, the sensor sheet comprising:
    a first adhesive sheet to be applied to a skin of a subject;
    a second adhesive sheet to be stuck to a front surface side of the first adhesive sheet; and
    an electric circuit comprising a plurality of electrodes and wires connected to the plurality of electrodes, the electric circuit provided in an area in the second adhesive sheet, wherein,
    the second adhesive sheet is thicker than the first adhesive sheet,
    the first adhesive sheet is higher in stretchability than the second adhesive sheet,-and
    the stretchability of a peripheral edge area of the second adhesive sheet is higher than that of a center area of the second adhesive sheet, and
    the sensor sheet further comprising slits formed in the peripheral edge area of the second adhesive sheet.

2. The sensor sheet according to claim 1, wherein the second adhesive sheet is smaller in area than the first adhesive sheet, and is stuck to a center area of the first adhesive sheet except a peripheral edge area of the first adhesive sheet.

3. The sensor sheet according to claim 1, wherein the first adhesive sheet contains polyurethane as a main component and has a thickness of no more than 20 μm.

4. The sensor sheet according to claim 1, wherein the second adhesive sheet is higher in strength than the first adhesive sheet.

5. The sensor sheet according to claim 1, wherein:
each of the wires has a meandering shape in a surface of the second adhesive sheet.

6. The sensor sheet according to claim 1, wherein:
each of the wires is formed on a film base material that is less flexible than the first and second adhesive sheets.

7. The sensor sheet according to claim 1, wherein the sensor sheet is used for continuous electrocardiogrameasurement for at least two weeks.

8. The sensor sheet according to claim 1, wherein the peripheral edge area of the second adhesive sheet is a buffer area having a stretchability that is lower than that of the first adhesive sheet and higher than that of the center area of the second adhesive sheet.

* * * * *